United States Patent
Friedli et al.

(10) Patent No.: US 8,728,060 B2
(45) Date of Patent: May 20, 2014

(54) INFUSION DEVICE PROVIDED WITH A WATER-TIGHT COVER

(75) Inventors: Kurt Friedli, Lyssach (CH); Ulrich Haueter, Grosshochstetten (CH)

(73) Assignee: Roche Diagnostics International AG, Steinhausen (CH)

( * ) Notice: Subject to any disclaimer, the term of this patent is extended or adjusted under 35 U.S.C. 154(b) by 381 days.

(21) Appl. No.: 13/165,200

(22) Filed: Jun. 21, 2011

(65) Prior Publication Data

US 2011/0247397 A1    Oct. 13, 2011

Related U.S. Application Data

(63) Continuation of application No. 11/912,492, filed as application No. PCT/EP2006/003836 on Apr. 25, 2006, now Pat. No. 7,988,687.

(30) Foreign Application Priority Data

Apr. 25, 2005 (EP) ..................................... 05009039

(51) Int. Cl.
*A61K 9/22* (2006.01)
(52) U.S. Cl.
USPC .................... 604/891.1; 604/890.1
(58) Field of Classification Search
USPC ............... 604/890.1, 891.1, 131, 151
See application file for complete search history.

(56) References Cited

U.S. PATENT DOCUMENTS

| | | | |
|---|---|---|---|
| 4,373,527 A | 2/1983 | Fischell | |
| 4,619,653 A | 10/1986 | Fischell | |
| 4,784,645 A * | 11/1988 | Fischell | ........................ 604/153 |
| 5,045,051 A | 9/1991 | Milder et al. | |
| 5,230,350 A * | 7/1993 | Fentress | ........................ 128/846 |
| 6,780,156 B2 | 8/2004 | Haueter et al. | |
| 2001/0025189 A1 | 9/2001 | Haueter et al. | |
| 2002/0077598 A1 | 6/2002 | Yap et al. | |
| 2005/0033148 A1 | 2/2005 | Haueter et al. | |
| 2006/0252977 A1* | 11/2006 | Sullivan | ........................ 600/16 |
| 2007/0123820 A1 | 5/2007 | Gafner-Geiser et al. | |

FOREIGN PATENT DOCUMENTS

| | | | |
|---|---|---|---|
| AU | 2003267022 A1 | 4/2004 |
| CA | 2496587 A1 | 3/2004 |
| DE | 10240165 A1 | 3/2004 |
| DE | 102004026805 A1 | 1/2006 |
| EP | 1486218 A2 | 12/2004 |
| WO | 0113785 A2 | 3/2001 |

OTHER PUBLICATIONS

International Search Report for PCT/EP2006/003836, dated Jul. 28, 2006.
European Search Report for EP 0500 9039, dated Nov. 3, 2005.

* cited by examiner

*Primary Examiner* — Laura Bouchelle
(74) *Attorney, Agent, or Firm* — Dinsmore & Shohl LLP

(57) ABSTRACT

The invention relates to an infusion device for therapeutic use comprising a water-tight cover in the form of a housing, a housing part or a receptacle for holding said infusion device and a control system which is used for controlling the cover water tightness and comprises c) a medium arranged in the cover and characterized by at least one physical or chemical quantity variable according to the cover water tightness and d) an information system which automatically transmits at least one information signal when said quantity changes in such a way that the loss of the cover water tightness is indicated.

15 Claims, 3 Drawing Sheets

INFUSION DEVICE PROVIDED WITH A WATER-TIGHT COVER

CROSS-REFERENCE TO RELATED APPLICATION(s)

Figure 1:
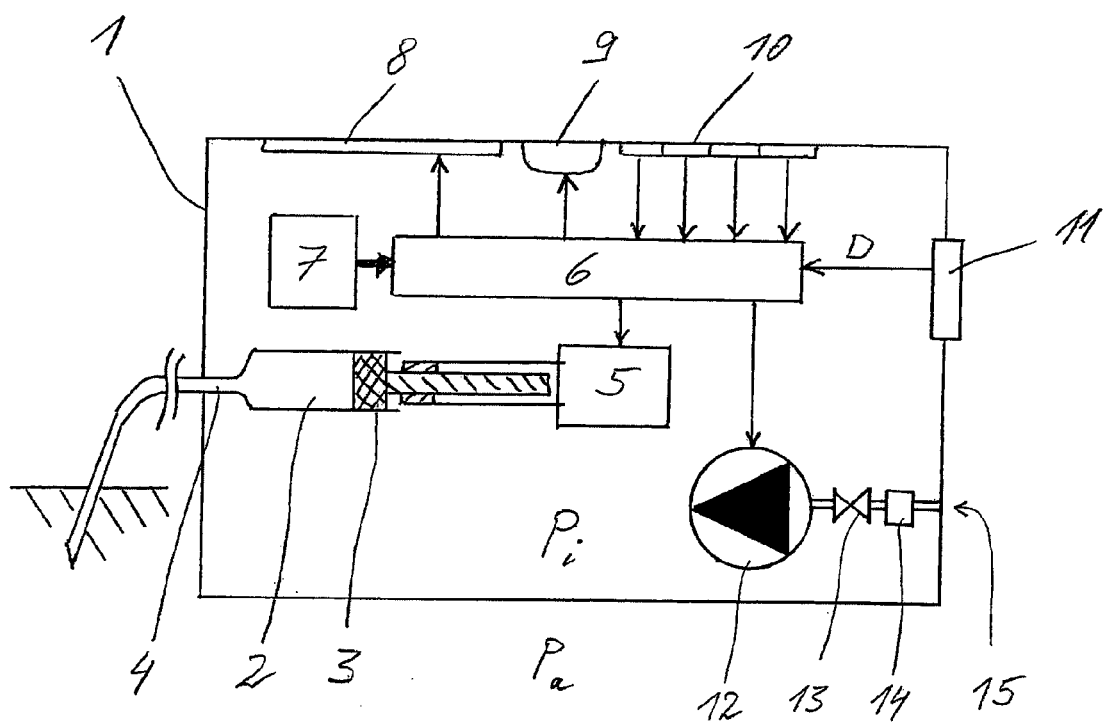

This application is a continuation application of U.S. application Ser. No. 11/912,492, filed 9 Jun. 2008, which is a Section 371 National Stage Application of International Application No. PCT/EP2006/003836, filed 25 Apr. 2006 and published as WO 2006/114288 A1 on 2 Nov. 2006, which claims the priority from the European Patent Application No. 05009039.8, filed 25 Apr. 2005.

The invention relates to infusion devices for therapeutic applications, preferably for self-administering medicines.

Typical examples of such infusion devices are insulin pumps such as are used in diabetes therapy. Most insulin pumps are supplied as waterproof devices. Guaranteeing the water-impermeability of the device as the service life of the devices increases—likely to increase even further in future—is problematic. If an infusion device is specified as being waterproof, its water-impermeability must be guaranteed for the entire service life of the device. Ensuring that each device leaves the production line waterproof is not technically problematic. However, as the service life of the devices increases, problems can arise through material fatigue alone, for example through unnoticed cracks in the casing. Greater problems arise due to the fact that such devices are often in operation 24 hours a day and can thus be exposed to particular stresses. The devices can for example be dropped, i.e. can experience impact stresses. After major mechanical stresses, in particular impact stresses, it is no longer possible to guarantee with the necessary assuredness that the relevant device is still waterproof. However, the entry of moisture can result in malfunctions or even the failure of a device. Administering the medicine in exact doses is thus jeopardized.

It is an object of the invention to counteract, at an early stage, faults in infusion devices for therapeutic applications due to the entry of moisture.

The invention proceeds on the basis of infusion devices for therapeutic applications such as are known in principle and do not therefore need to be described in more detail. Such an infusion device can for example be designed like known insulin pumps which are used in diabetes therapy for self-administering insulin. Such an insulin pump also represents a preferred example of an infusion device in accordance with the invention. The invention is not, however, limited to administering insulin, but extends generally to administering products which can be administered by infusion. The infusion device is an external device which can preferably be worn or carried on the body, for example on and in contact with the skin, or in clothing. The invention is primarily, though not exclusively, directed to portable devices for self-administering. Comparable devices can however also be used in a stationary environment, for example in hospitals or clinics under the constant watch of a physician, for example in rehabilitation or other follow-up treatments, in which they are worn or carried on the body by patients.

The infusion device is fitted with a waterproof covering. The covering can in particular form the casing of the infusion device, which mounts and water-impermeably envelops a conveying means for the product to be administered, the necessary control and as applicable regulating components, and an operating means and in most cases an optical display. The covering can also form only a part of the casing, in which one or more water-sensitive components is/are accommodated. The waterproof covering can however also merely form a waterproof container for storing the infusion device, wherein in this case, the infusion device itself preferably comprises—though need not comprise—a waterproof casing. Waterproof storage containers are intended for use in water, for example for swimming, in order as securely as possible to prevent the entry of moisture. Such an additional storage container, if provided, is deemed to form part of the infusion device in the sense of the invention.

The infusion device is also fitted with a monitoring means, by means of which the water-impermeability of the covering is monitored. The monitoring means is based on a medium and in this sense comprises a medium which is situated in the covering and characterized by at least one physical or chemical parameter which changes in accordance with the impermeability, i.e. the water-impermeability or preferably even the gas-impermeability, of the covering. The medium differs from the ambient air in at least this one physical or chemical parameter.

The monitoring means also comprises an information means which, if said parameter changes, automatically outputs an information signal, at least when the extent of the change in the parameter, viewed as an absolute or percentage value, signifies a loss of water-impermeability in the covering. A loss of water-impermeability is signified if there is a danger that water or water vapor from the device's surroundings, if present, is penetrating through the covering. This is intended to include the case in which water has already entered and is detected as such, or a consequence of it penetrating is detected; however, the danger of water entering is preferably detected preventatively, before it has actually penetrated. The danger of water penetrating or of an actual penetration is appropriately indicated by information signal.

The medium can in particular be a fluid, preferably a gas, which fills the inner space enveloped by the covering. A non-water vapor can be used as applicable, which the term "gas" when used in the following is intended to encompass. The covering can be formed with multiple walls, in particular a double wall, and in such an embodiment of the covering, the fluid can fill the inner space formed in the covering itself and enclosed between two adjacent walls of the covering, and can form a layer of the covering, so to speak. The medium need not be a fluid, but can also for example be formed by a solid layer of the covering or by a sufficient density of particles embedded in the other material of the covering, wherein said layer or particles experience a change in a physical or chemical parameter which characterizes them, when they come into contact with moisture. The parameter can for example be their electrical conductivity. As mentioned, however, it is preferred if a fluid forms the medium and simply fills the inner space as a whole, which is enveloped by the covering which can have multiple walls but preferably simply has one wall.

The physical or chemical parameter which characterizes the fluid is preferably the fluid pressure, in that the fluid in the inner space exhibits a different pressure to the air surrounding the covering on the outside. Both a positive pressure difference, i.e. a pressure burden in the inner space, and a negative pressure difference with respect to the surroundings are suitable in principle. A pressure burden in the inner space has the advantage not only that a leak can be detected by a drop in pressure, but the pressure burden itself can preventatively counteract the entry of water or water vapor. A partial vacuum in the inner space also enables leaks to be detected, but tends to promote the entry of moisture. The differential pressure, preferably a positive differential pressure, should be between 0.1 and 1 bar. Preferred differential pressures are between 0.3 and 1 bar, even more preferably between 0.4 and 0.8 bars.

In a first embodiment, the differential pressure is permanently maintained. The monitoring means comprises a corresponding pressure means for maintaining the differential pressure. The pressure means preferably operates such that, if the pressure reaches or falls below a predetermined minimum differential pressure, the pressure means returns the pressure in the inner space to a predetermined maximum differential pressure. The pressure means preferably automatically ensures that the differential pressure is maintained, i.e. it automatically ensures that the pressure never falls in the direction of pressure equilibrium below a predetermined minimum differential pressure of for example 0.1 bars or slightly below.

In one variant, in which no attention is paid to permanently maintaining a minimum differential pressure, the differential pressure is automatically generated in predetermined time intervals. When the differential pressure is built up, it is monitored—likewise automatically—over a predetermined time interval by means of a pressure detector. Maintaining and monitoring the pressure automatically and permanently is, however, preferred to this variant.

In a second embodiment, the pressure difference is generated by manually activating an operating element or activating element, i.e. "on demand", and/or automatically when performing operating steps which have to be performed. Removing and/or inserting a reservoir or battery can then for example automatically activate a pump. Once the pressure difference has been set, the impermeability is checked, either automatically when a predetermined differential pressure is reached, or when an operating element is activated. The pressure means can be one which is to be manually activated by means of an activating element, in particular a mechanical pump in which the pump movement is performed manually, for example by pressing a pump key which is integrated into the covering and water-impermeably, preferably gas-impermeably, sealed off from the outside. In one variant, the pressure means can operate semi-manually and semi-automatically, in that manually activating an operating element causes the pressure to be generated, for example by means of a mechanical, externally driven pump, a pressure reservoir or other means for generating the pressure. In the second embodiment, in which the pressure means is manually activated or manually triggered by means of an operating element, it is likewise possible to ensure that a differential pressure is permanently maintained, by indicating to the user through a signal that the pressure has fallen below a minimum differential pressure, which however requires the pressure in the inner space to be correspondingly monitored. Manually activating or triggering the pressure means, with the result that a pressure burden is generated, can in particular be used preventatively when the user of the device knows that he will shortly be coming into contact with water, for example because he wishes to go swimming or to shower but does not wish to take the infusion device off.

In both embodiments, including the variants, the pressure in the inner space is monitored. It is preferably monitored constantly or automatically at predetermined time intervals, wherein it is established whether the pressure difference is dropping faster than would be expected if the covering were intact. In the second embodiment and the variant of the first embodiment, however, it is also completely sufficient if the pressure is only ever monitored directly after the pressure is generated for a predetermined time interval, wherein monitoring is preferably automatically coupled to generating the pressure. Even in the first embodiment in which the differential pressure is permanently maintained, it is in principle sufficient to periodically or non-periodically monitor the pressure, preferably automatically, as long as the time intervals between the individual phases of monitoring the pressure are small enough for impermeability to be established early.

The differential pressure can be permanently maintained or constantly regenerated in different ways. The differential pressure can in particular be maintained or generated electrothermally, electrochemically, mechanically, chemically or by means of a swelling material. Maintaining or generating the pressure using a combination of two or more methods, in particular a combination of two or more of the aforesaid methods, is also conceivable.

A mechanical method can be performed by means of a pump, or realized by providing a pressure reservoir. A mechanical pump for generating a partial vacuum or preferably a pressure burden in the inner space, which pumps air out of the inner space into the surroundings or preferably from the surroundings into the inner space, requires an air connection which must be sealed, for example by means of a corresponding valve, in order to guarantee the required impermeability of the covering. A pressure reservoir, by contrast, can be arranged within the waterproof covering and does not impair its impermeability, but could on the other hand possibly shorten the service life of the infusion device or necessitate maintenance in which the pressure reservoir is exchanged for a new one. The mechanical pump can be one which can be connected to the cited air connection from the outside.

In a preferred embodiment using a mechanical pump, however, said pump is arranged in the inner space of the covering. If the differential pressure is to be automatically maintained or generated, and the pump is arranged in the inner space, then the drive provided for conveying the product can also be used as a drive of the pump for maintaining or generating the differential pressure, though alternatively, an additional drive can also be provided. As already mentioned, a manually activated mechanical pump is preferably activated by pressing a push key spanned on the outside by a part of the covering which is flexible in the pressing direction, for example a flexible film. The mechanical pump can for example be designed as a simple air pump for pumping up tires, only miniaturized, or like the pumps in spray cans.

Electrochemically generating the pressure in order to maintain a pressure burden in the inner space of the covering is based on at least one element which can generate a defined amount of a gas. A plurality of such elements can be arranged in the inner space. The gas cell system is particularly suitable as such an element. A gas cell is an element which is arranged in a circuit and, when the circuit is closed, produces hydrogen gas or another gas. The amount of gas produced is proportional to the current flowing through the cell. Such elements are for example known from automatic lubricating systems under the keyword "greasers".

In other embodiments of the invention, in which the medium is a fluid, preferably a gas, the concentration of the fluid serves as the physical or mechanical parameter characterizing the medium. The composition of the fluid must of course differ from that of air, for example by being a pure fluid or a fluid mixture which can be distinguished from air. If the fluid is a fluid mixture, then the concentration of a single constituent of the mixture can form the parameter. The concentration of one constituent—or the concentrations of a number of the constituents—of air can also serve as the characterizing parameter, if the concentration or concentrations is/are increased or can only be established in the first place when there is penetration of air. The same applies analogously when using a pure fluid. Loss of fluid or of a fluid constituent can in particular be compensated for electrothermally, electrochemically or chemically, or also by arranging a pressure reservoir containing the fluid in the inner space. Gaseous nitrogen would for example be appropriate as such a fluid, the concentration of which is monitored in the inner space. In the embodiments in which a fluid which differs in its composition from air, i.e. a pure-type fluid or a fluid mixture, forms the medium, maintaining a permanent pressure burden in the inner space is also preferred to a partial vacuum or pressure equilibrium with the surroundings, in order to preventatively counteract the penetration of moisture.

In preferred embodiments, the monitoring means also comprises a detector for the at least one characterizing physical or chemical parameter, in particular in embodiments in which a pressure difference and/or pressure gradient or the concentration of a fluid or fluid constituent forms the parameter. The output of the detector is connected to the information means. The detector feeds a detection signal to the information means, from which the information means forms the information signal. The detector can in particular be an integral component of the covering. In preferred embodiments, it forms a planar region of the covering, for example if it is a differential pressure detector. An elastic membrane or wire strain gauge can in particular form a sensor element of such a differential pressure detector. The membrane must of course be waterproof; it is preferably air-tight. If the medium is a gas which diffuses more easily than air, or contains a constituent which diffuses more easily than air, then the membrane should also be impermeable to the relevant gas or gas constituent having the greatest diffusion coefficient.

If the concentration of a fluid filling the inner space or the concentration of a constituent of such a fluid forms the characterizing parameter by itself or in conjunction with another parameter, preferably the pressure, then an oxygen-free fluid should be used. The penetration of air can then be established by means of an oxygen sensor. The oxygen sensor preferably establishes not only whether the concentration of oxygen in the inner space differs from the value zero, but also whether it has simply only exceeded an absolute threshold value or has exceeded it within a predetermined time interval.

Other ways of monitoring the impermeability include directly detecting moisture by means of a moisture detector or using a medium which chemically reacts with water or air—for example the oxygen contained in the air—wherein the chemical reaction and the reaction products should be harmless to the infusion device itself. If the permeability is detected via a chemical reaction, then a detector could for example be formed by a thermal sensor. If the permeability is to be detected directly by means of a moisture detector, then it would be appropriate to use a moisture-bonding medium, which would simultaneously entail an advantageous preventative effect, i.e. if the moisture-bonding medium and the moisture detector are adjusted to each other, such that the permeability is detected before a dangerous degree of moisture is reached in the inner space. A suitable medium for bonding moisture is for example silicone gel.

If a medium is used which shows a change in color when moisture, i.e. water or water vapor, or air is present, then the use of an additional detector can be dispensed with and the change in color can itself directly form the information signal. The medium itself then forms the detector.

Systems based on an additional detector with a signal output are, however, preferred. As an alternative to the detectors for pressure as already cited, including deformation detectors, concentration, moisture and heat, or in addition to such a detector, it is possible to provide a detector which simultaneously forms the medium and comprises a signal output. The medium and the detector can then be formed by a layer of the covering or by particles embedded in the covering, the electrical conductivity or capacitance or inductivity of which changes when they come into contact with moisture and is monitored as the physical parameter. As already mentioned elsewhere, however, it must be ensured that such a detector medium is provided in a sufficient density over the entire covering.

The information signal can be an optical, acoustic or tactile signal or a combination of a number of these types of signal. An optical information signal can for example be indicated on a display, such as is usually provided on infusion devices, or by means of an additional light source, for example an LED, and should be outputted as a flashing signal. In order to generate a tactile signal, a vibrator can for example be provided. A combination of an optical indication on a display and an acoustic or tactile signal, or a combination of an acoustic and a tactile signal, is preferred. Combined information signals provide the greatest assuredness that the user will notice the permeability and clearly identify it as the cause.

Other preferred features of the invention are disclosed in the sub-claims and by the combinations of claims described by means of the sub-claims.

Repeated reference has been made above to the advantages of preventative measures, i.e. maintaining a permanent pressure burden or arranging a moisture bonder in the inner space. A combination of the two measures is also advantageous in order to reduce this risk. The Applicant reserves the right to direct an application to the preventative measures, irrespective of whether—in addition to the preventative measures—impermeability is monitored or not. With respect to such another application, however, reference is also made to the fact that the combination of preventative measures and monitoring is deemed to be particularly advantageous.

In one development, a pressure burden existing in the covering performs the work necessary in order to convey the product to be administered. The pressure burden can be set in a regulated manner, such that it conveys the product at exactly the desired conveying rate. By adjusting the pressure burden to the conveying characteristics of the mechanical element or elements of the conveying means, it is possible to set a constant conveying rate and in principle also a varying conveying rate, wherein however the latter requires that the pressure burden can also, if necessary, be rapidly released by means of a release valve which is impermeable to water and preferably impermeable to water vapor. However, it is preferred if the pressure burden is generated and maintained as described, and large enough that it is sufficient for conveying the product at any conveying rate necessary for the respective therapy. A pressure burden in the range of 0.5 to 5 bars should be sufficient for this purpose.

If a piston driven by means of the pressure burden, preferably a reciprocating piston, or another conveying member which can be moved in a reservoir is used as the mechanical conveying member, the pressure burden is advantageously set to at least 2 bars. On the other hand, such a pressure burden conveying means should be designed such that the pressure burden necessary for driving the conveying member is as small as possible and preferably 4 bars at most, or even more preferably 3 bars at most. If the product is conveyed by means of one or more pistons, it is advantageous if the piston area on which the pressure burden acts is large. A container forming the reservoir can then for example be designed very flat in the direction of advancing the piston, as compared to at least one of its dimensions transverse to the advancing direction, such that the side wall of such a container which is round all over—or the number of side walls of such a container which form edges—and extend(s) in the advancing direction is/are substantially smaller in relation to the piston area on which the pressure burden acts than in conventional product containers, for example cylindrical ampoules, such as are generally used for example in diabetes therapy. Such a conveying means can get by on a comparatively small pressure burden of less than 2 bars. A particularly preferred container of this type is described in German patent application No. 10 2004 026 805.3, which is hereby referenced.

In alternative embodiments, a container which accommodates the product forms the conveying member of the conveying means itself. In such embodiments, the container can be deformed, i.e. compressed by means of the pressure burden. Due to the effect of the pressure burden and the resultant reduction in the inner volume of the flexible container, the product is displaced from the container and delivered. The container can then in particular be formed by a pouch. Instead of configuring the container such that its entire volume enveloping the product is flexible, it is also possible to use a container which is formed by a combination of at least one rigid container wall and at least one flexible container wall which is fixedly connected to it. When using a deformable container as the conveying member, the pressure burden cited in connection with the impermeability problem is also sufficient for the purposes of conveying the product.

In an advantageous development, a dosing means is used in combination with a pressure burden conveying means, into which the non-dosed product is conveyed by means of the pressure burden.

The dosing means can be a simple blocking unit which is arranged in the outlet of the reservoir or downstream of the outlet in a cannula and is directed by the controller to close and open the outlet or cannula cross-section.

However, it is preferred if the dosing means forms an additional conveying means which measures out the product, supplied by means of the pressure burden conveying means, into small portions and conveys the exactly measured-out product portions further. The product portions formed by the dosing means are administered. In such an embodiment, the dosing means forms a dosing chamber having a definitive chamber volume. The pressure burden conveying means, which advantageously no longer has to be connected to the controller, conveys the product into the dosing chamber, and the dosing means conveys the product amount predetermined by the dosing chamber volume, portion by portion, from the dosing chamber into the cannula section connected to the dosing chamber. The conveying rate is determined by means of the size of the chamber volume and the clock frequency of an expelling element of the dosing means. Examples of suitable dosing means are peristaltic pumps, other crimp pumps and in particular also piston pumps.

Figure 2:
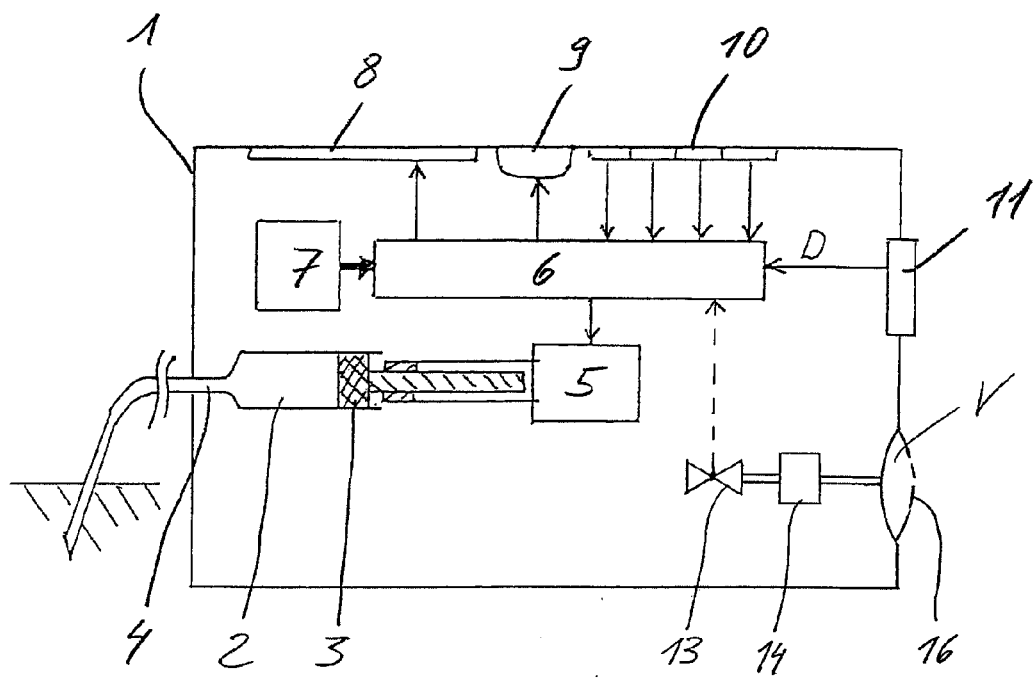
Figure 3:
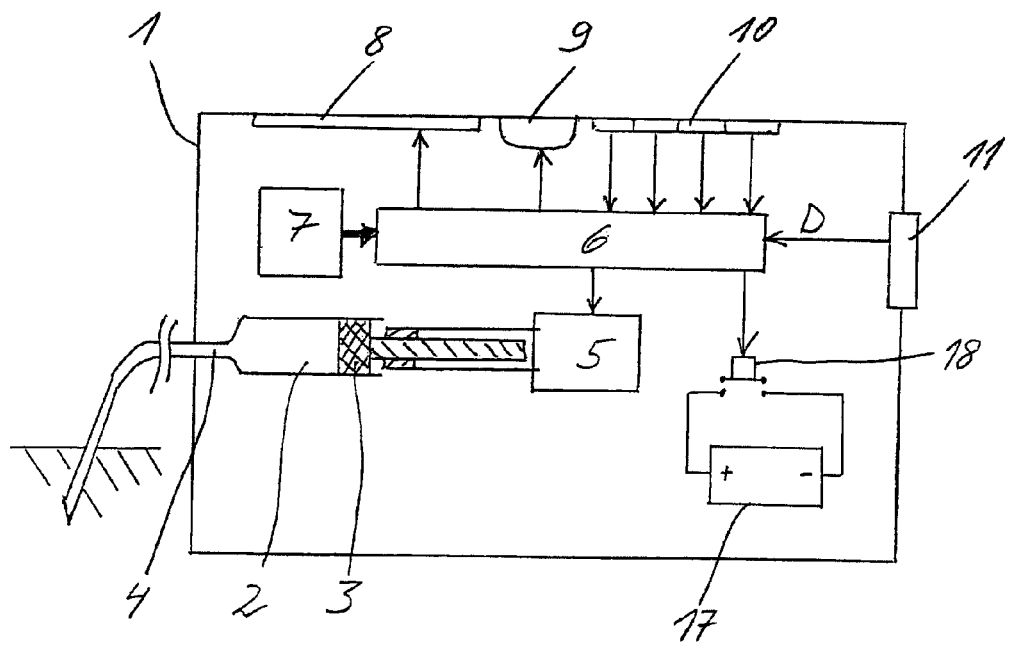
Figure 4:
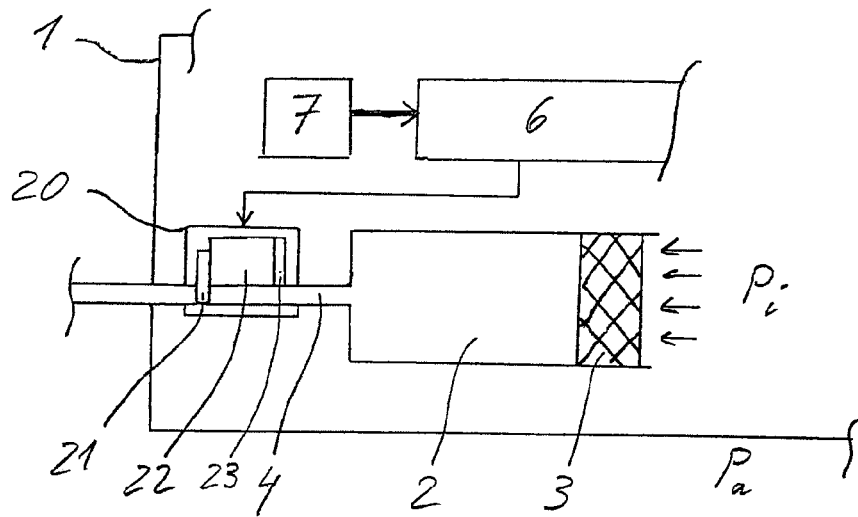
Figure 5:
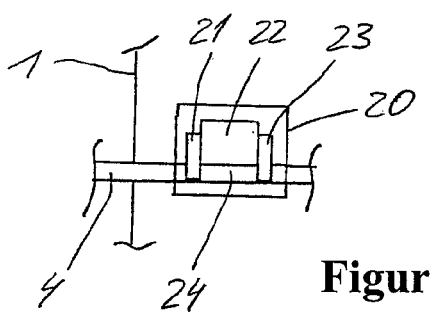
Figure 6:
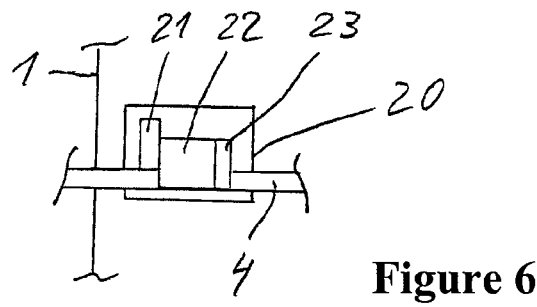

The invention is explained below on the basis of example embodiments. Features disclosed by the example embodiments, each individually and in any combination, develop the subjects of the claims and also the features of the invention described above in advantageous directions. There is shown:

FIG. 1 an infusion device with a waterproof covering and a monitoring means, according to a first example embodiment;

FIG. 2 an infusion device with a waterproof covering and a monitoring means, according to a second example embodiment;

FIG. 3 an infusion device with a waterproof covering and a monitoring means, according to a third example embodiment;

FIG. 4 an infusion device with a pressure burden conveying means and a dosing means, in a first switched state;

FIG. 5 the dosing means of FIG. 4, in a second switched state;

FIG. 6 the dosing means of FIGS. 4 and 5, in a third switched state; and

Figure 7:
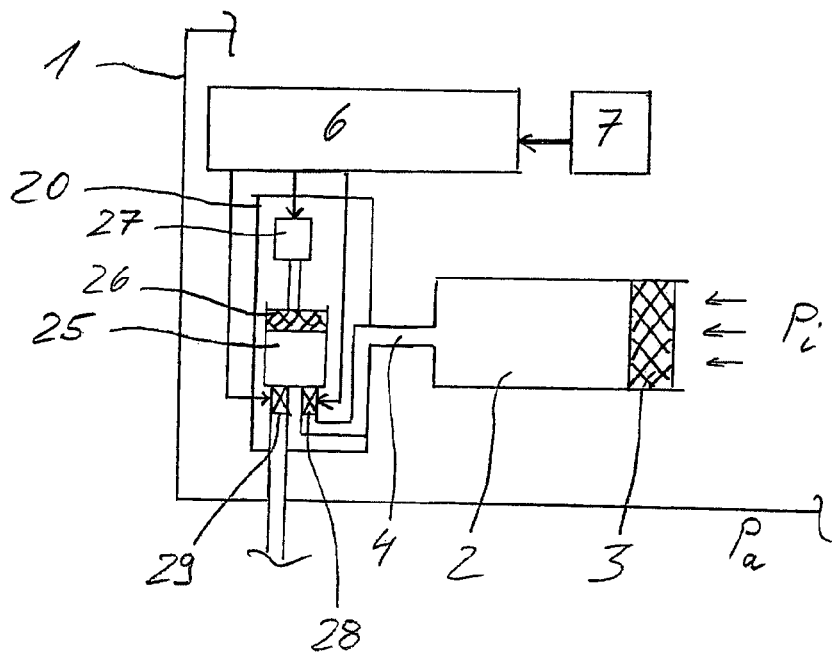

FIG. 7 an infusion device with a pressure burden conveying means and a different dosing means.

FIG. 1 shows an infusion device comprising a casing which forms a waterproof covering 1 in which all the components of the device are accommodated. The covering 1 encloses: a reservoir 2 which is filled with a product to be administered; a conveying means; a monitoring means; and an indicating and operating means. The conveying means comprises: a piston 3 which is accommodated in the reservoir 2; a motor 5; a gear, via which the motor 5 is coupled to the piston 3 by means of a piston rod, in order to drive the piston 3; a controller 6 for the motor 5 which also comprises power electronics for the motor 5; and an energy source 7 for the conveying means and any other components of the infusion device which are to be supplied with energy. A flexible cannula 4 is guided through the covering 1, with the necessary seal, and is connected at one end to an outlet of the reservoir 2 and attached at the other end to an infusion cannula. For subcutaneously administering the product, the infusion cannula protrudes under a patient's skin. The infusion cannula can also project directly out of the covering 1 by only the length which is inserted into the tissue, in order to attach the covering 1 directly on the skin. For administering, the motor 5 is directed by the controller 6 in accordance with predetermined programming. Via a reducing gear, the motor 5 drives the piston rod, and together with it the piston 3, in an advancing direction towards the outlet of the reservoir 2, such that product is displaced from the reservoir 2 and subcutaneously administered in accordance with the piston movement. The controller 6 can in particular comprise a processor and one or more associated program memories and preferably also data memories.

The indicating and operating means comprises an optical display 8, an acoustic signal transmitter 9 and a keyboard in the form of a keypad 10 with input keys and operating keys. The covering 1 is transparent in the region of the display 8. The acoustic signal transmitter 9 and the keypad 10 are integrated into the covering 1 such that an acoustic signal can be emitted and the keys of the keypad 10 can be pressed, but on the other hand, these regions are impermeable to water. The display 8 can also be formed as a touch screen, such that a separate keypad can be dispensed with.

The water-impermeability of the covering 1 is permanently monitored. A pressure $P_i$ which prevails in the inner space enveloped by the covering 1 is greater than the atmospheric pressure $P_a$ on the outer surface of the covering 1. The pressure $P_i$ in the inner space, or more specifically the differential pressure $P_i-P_a$ is constantly monitored. For monitoring, the infusion device is fitted with the monitoring means, some of whose components are arranged in the inner space of the covering 1 and the rest of which are an integral component of the covering. To this extent, a pressurized gas—in the example embodiment, air—which fills the inner space of the covering 1 and is pressurized to $P_i$ also counts as the monitoring means. The pressure burden $P_i$ not only enables the impermeability to be monitored by monitoring the pressure $P_i$ or the differential pressure $P_i-P_a$, but is simultaneously also an advantageous preventative measure against the penetration of moisture in the form of water or water vapor from the outer surroundings.

The monitoring means also comprises an information means and a pressure difference detector 11, the output signal of which is fed to the controller 6 as a detection signal D, for the controller 6 not only has the task of directing the motor 5, the display 8 and the acoustic signal transmitter 9 to control the conveying action and output the relevant information signals, including alarm signals, via the display 8 and the acoustic signal transmitter 9, but rather a part of the controller 6 simultaneously also forms a component of the monitoring means. To the extent that the display 8 and the signal transmitter 9 are used within the framework of monitoring, they also form part of the monitoring means for the impermeability and, together with the part of the controller 6 serving to monitor the impermeability, form the information means of the monitoring means. The differential pressure detector 11 comprises an airtight, elastic membrane which forms a sensor element of the detector 11. The membrane is connected, airtight and elastically tensed, to the fixed structure of the covering 1 which encloses it. It bulges slightly outwards due to the differential pressure $P_i-P_a$. The membrane can itself be designed for example as a wire strain gauge. Wire strain gauges can likewise be embedded in or attached to an elastic membrane material.

The controller 6, i.e. the part of the controller 6 forming part of the monitoring means, identifies whether the covering 1 is still impermeable or is no longer impermeable, on the basis of a comparison between the value of the detection signal D and a predetermined comparison value.

Since a 100% impermeability to air cannot in practice be ensured, the monitoring means also comprises a pump 12 which is connected to the surroundings by an air connection 15 which is integrated in the covering 1. A closure unit 13, for example a simple reflux valve, is arranged in the connecting conduit between the air connection 15 and the pump 12 and prevents a flow of air out of the inner space through the covering 1 into the surroundings, and so maintains the impermeability to air of the covering 1. A water barrier 14 is also arranged in the connecting conduit, which preferably also blocks the connecting conduit against the penetration of water vapor.

The controller 6 also controls and regulates the pump 12 and comprises power electronics for the pump 12. The energy source 7 also provides the energy for operating the detector 11 and the pump 12. This is indicated by the connecting conduit between the energy source 7 and the controller 6. The controller 6 controls the pump 12 in accordance with the value of the detection signal D. In sufficiently short time intervals, the controller 6 compares the value of the detection signal D with the predetermined comparison value which represents a predetermined minimum pressure burden in the inner space which the pressure is not to fall below. If the measured pressure burden $P_i$ reaches this minimum value, the pump 12 is directed to convey air from the surroundings into the inner space, until the inner pressure $P_i$ has reached a predetermined maximum value. As soon as the inner pressure $P_i$ has reached this maximum value due to the conveying action of the pump 12, which the controller 6 identifies on the basis of a comparison between the value of the detection signal D and the maximum value, the controller 6 switches the pump 12 off. This ensures that a pressure burden $P_i$ permanently prevails within the covering 1, but can fluctuate between the predetermined maximum value and the predetermined minimum value.

In order to be able to identify a loss of water-impermeability in the covering 1, the controller 6 also takes into account the time which has elapsed when a drop in pressure is established. If the time interval in which an established loss of pressure has occurred falls below a predetermined time interval, then this signifies a loss of water-impermeability. In this case, the controller 6 directs the acoustic signal transmitter 9 in a characteristic way, such that the signal transmitter 9 outputs an acoustic alarm signal which characterizes the loss of water-impermeability. The controller 6 also directs the display 8 in a characteristic way, in order to also indicate the loss of water-impermeability optically.

FIG. 2 shows an infusion device in a second example embodiment which differs from the infusion device of the first example embodiment in that instead of a motorized pump, it comprises a pump 16 which is to be activated manually and which only operates when it is activated. The pump 16 is manually activated like a push key. It comprises an elastic outer membrane which is perforated in a middle planar region, but otherwise seals off a pump volume V of the pump from the outside, airtight. By pressing the outer membrane, the middle region of the outer membrane is sealed off by the user's fingertip and the volume V is pumped through the downstream water barrier 14 and the closure unit 13, into the covering 1. The reflux valve 13 prevents gas from the covering being suctioned into the pump volume. The water and water vapor barrier 14 is likewise provided again. Monitoring the pressure can be coupled to activating the pump 16, such that it only begins when or immediately after the pump 16 is activated and is then for example switched off again when a predetermined differential pressure is reached and after it has been indicated. This operating mode serves to save energy. Alternatively, however, the pressure can instead also be monitored constantly. Toggling between the two modes, for example on the keypad 10, is also conceivable. The broken line indicates the alternative whereby the closure unit 13 informs the controller 6 that a predetermined differential pressure $P_i-P_a$ has been reached. The closure unit 13 can then for example be formed as a pressure limiting valve which, when the predetermined differential pressure is reached, automatically releases the backflow into the volume V of the pump 16 and thus into the surroundings, such that only the differential pressure $P_i-P_a$ predetermined by the pressure limiting valve 13 can be generated using the pump 16. As soon as the closure unit 13 releases the backflow, it sends a corresponding signal to the controller 6, which indicates— via the signal transmitter 9 and/or the display 8—that the predetermined differential pressure or nominal pressure has been reached, and the user can discontinue the pumping process. Although the inner pressure $P_i$ is periodically or preferably constantly monitored by means of the detector 11 and, if the pressure falls below a minimum value, an indication is outputted via 8 or 9, it is generally possible to dispense with such monitoring in a simple embodiment, and also with the detector 11. In such an embodiment, the generated positive differential pressure $P_i-P_a$ is used purely as a preventative measure against the penetration of moisture.

The third example embodiment of an infusion device, shown in FIG. 3, differs from the first example embodiment only in the means for maintaining a permanent pressure burden $P_i$ in the inner space of the covering 1. The mechanical pump of the first example embodiment is replaced in the third example embodiment by a gas cell 17 or an array of multiple gas cells 17 which generate(s) a gas, for example $H_2$ gas, electrochemically. The at least one gas cell 17 is arranged in an electrical circuit with a switch 18. The switch 18 is connected to the controller 6. If the differential pressure $P_i-P_a$ measured by means of the detector 11 falls below the minimum value, the controller 6 closes the electrical circuit by means of the switch 18, and the at least one gas cell 17 releases gas. The switch 18 is held in its closed position against an elastic restoring force until the differential pressure has reached the maximum value. The gas cell 17 or gas cell array is preferably integrated in or held inside an exchangeable casing part, for example a lid, or an adaptor which is detachably connected to the casing.

Aside from the differences described, the second and third example embodiments correspond to the first example embodiment.

The minimum value of the differential pressure $P_i-P_a$ is preferably selected from a range of 0.1 to 0.5 bars. The maximum value is preferably selected from a range of 0.4 to 1 bar. Instead of a differential pressure sensor, the detector 11 can also merely be an inner pressure sensor. In this case, an absolute inner pressure $P_i$ in the covering 1 is monitored, the minimum value of which is preferably selected from a range of 1.1 to 1.5 bars and the maximum value of which is preferably selected from a range of 1.4 to 2 bars and of course greater than the minimum value.

The inner space of the covering 1 can be connected to the surroundings via a pressure limiting valve which can be formed by the closure unit 13, in order to partly release a pressure burden prevailing in the inner space. This can be advantageous inter alia when a high absolute pressure prevails in the inner space of the covering 1—due to a temporarily high ambient pressure, such as can occur when diving, and because a differential pressure $P_i-P_a$ has been set—which could result in an undesirable delivery of product after emerging. By means of the pressure limiting valve, the inner pressure is returned to the predetermined range for the differential pressure or to the absolute pressure.

FIG. 4 shows a part of an infusion device which, apart from the differences described below, can in particular be designed like the infusion devices already described.

The conveying means comprises a simple pressure burden conveying means and a dosing means 20. The fluid in the inner space of the covering 1, pressurized to $P_i-P_a$, forms the working medium of the pressure burden conveying means. The piston 3 arranged in the reservoir 2 forms the only mechanically fixed conveying member of the conveying means. The inner pressure $P_i$ acts directly on the rear side of the piston 3, in the direction towards the outlet of the reservoir 2.

The pressure burden $P_i-P_a$ is set to at least 2 bars for advancing the piston 3. A pressure burden of about 3 bars, or as applicable an even greater pressure burden, is advantageous. If the pressure burden is to be smaller, in order for example to keep the energy required for generating the pressure and/or the size of the pressure generating means small, then alternative embodiments use a reservoir which can be compressed by the prevailing pressure burden, i.e. a sufficiently flexible container, instead of a conveying means based on the action of a conveying piston or other mechanical conveying member. The reservoir 2 can then in particular be replaced by a pouch which is deformed by the pressure burden prevailing in the covering 1, such that its volume is reduced and the product is thus displaced from the reservoir which is flexible in this way. In such embodiments, the pressure burden of 1 bar already mentioned elsewhere, or more preferably an even smaller pressure burden, is also sufficient for conveying the product.

The pressure burden or differential pressure $P_i-P_a$ is selected to be large enough that it would convey the product out of the reservoir 2 at a conveying rate which is greater than the desired conveying rate. The differential pressure is for example 1 bar if a container, for example a pouch, which can be deformed by the prevailing pressure burden forms the reservoir 2. If a mechanical conveying member, for example a piston 3 or as applicable a paddle wheel driven by the pressure burden, forms the conveying member, the differential pressure can be at least 2 bars, preferably about 3 bars.

In order to set the conveying rate in accordance with a therapy, for example a basal rate or a special bolus, the dosing means 20 is arranged downstream of the reservoir 2. The dosing means 20 is formed as a peristaltic pump which acts on a section of the flexible cannula 4 within the covering 1. The dosing means 20 comprises three crimping elements 21, 22 and 23 which are arranged in a row along the cannula 4 in the conveying direction and crimp the cannula 4 in a known way. Each of the crimping elements 21 to 23 can be moved back and forth between a first position and a second position. In the first position in each case, the relevant crimping element 21, 22 or 23 does not exert a crimping force on the cannula 4. In the second position in each case, the cannula 4 is crimped tight. The controller 6 directs the crimping elements 21-23 individually into either the first or second position. In the switched state in FIG. 4, the most downstream crimping element 21 assumes the second position, i.e. it crimps and thus closes the cannula 4. The most upstream crimping element 23 and the middle crimping element 22 each assume their first position. The pressure burden conveying means thus conveys the product as far as the crimping element 21. The inner pressure $P_i$ prevails in the cannula 4 up to the crimping point, which guarantees a complete expansion of the flexible cannula 4.

FIG. 5 shows the dosing means 20 in a second switched state which immediately follows the first switched state shown in FIG. 4. The crimping element 21 is crimping and thus still closing the cannula 4. As compared to the first switched state, the crimping element 23 has also been moved into the second position, such that the cannula 4 is closed tight at a second crimping point. Between the two crimping points, the cannula 4 forms a dosing chamber 24 having a chamber volume which is predetermined by the cannula section and the distance between the crimping elements 21 and 23. The middle crimping element 22 assumes its first position.

FIG. 6 shows the dosing means 20 in a third switched state which follows the second switched state, in that the crimping element 21 is moved into its first position and then the middle crimping element 22 is moved into its second position, i.e. its crimping position. Opening the flow cross-section of the cannula 4 and crimping together the dosing chamber 24 expels the product situated in the dosing chamber 24 and delivers a product amount corresponding to the chamber volume. The controller 6 then directs the dosing means 20 back into the first switched state, by moving the crimping element 21 back into its second position in a first step, and then moving the crimping elements 22 and 23 into their respective first positions. The controller 6 determines the conveying rate using the clock frequency at which the dosing means 20 is moved from the first switched state to the third switched state and back into the first switched state.

FIG. 7 shows an infusion device comprising an alternative dosing means 20. Apart from the differences described below, the statements made with respect to the infusion device of FIGS. 4 to 6 apply.

The dosing means 20 of the example embodiment in FIG. 7 is formed as a piston pump. The dosing means 20 comprises a dosing chamber 25, a piston 26 arranged in the dosing chamber 25, a drive 27 and two blocking units 28 and 29. The controller 6 controls the drive 27 and the blocking units 28 and 29. The piston 26 can be moved back and forth in the dosing chamber 25 between two end positions. The drive 27 is coupled to the piston 26 via a piston rod and moves it. The drive and the coupling to the piston 26 are configured such that the drive 27 moves the piston from each of the two end positions to the other end position in each case. Alternatively, the drive 27 and the coupling can also be formed as a restraining and restoring means, if the piston 26 is moved towards the outlet of the dosing chamber 25 by the pressure burden $P_i-P_a$ prevailing in the inner space of the covering 1.

A first section of the cannula 4 connects the reservoir 2 to the dosing chamber 25, and a second section of the cannula 4 connects to an outlet of the dosing chamber 25 and guides the product up to the point of administering. The blocking unit 28 closes and opens the section of the cannula 4 which connects the reservoir 2 to the dosing chamber 25, in accordance with the control signals of the controller 6. The blocking unit 28 is preferably positioned directly at an inlet into the dosing chamber 25. The blocking unit 29 is preferably positioned directly at the outlet of the dosing chamber 25.

When the dosing means 20 is in a first switched state, the inlet of the dosing chamber 25 is open and the outlet is closed. The differential pressure $P_i-P_a$ conveys the product from the reservoir 2 into the dosing chamber 25, thus filling it. In order to further convey the product, the controller 6 moves the dosing means 20 into a second switched state by blocking the inlet of the dosing chamber 25 using the blocking unit 28 and opening the outlet 29 by means of the blocking unit 29 which was previously in its closed state. In the second switched state, the drive 27 moves the piston 26 towards the outlet, or the piston 26 is moved towards the outlet by the differential pressure, such that a product amount corresponding to the chamber volume of the dosing chamber 25 is displaced and delivered. The controller 6 then reverses the drive 27, and the drive 27 moves the piston 26 back into the initial position shown in FIG. 7. During this resetting movement, the blocking unit 28 is opened and the blocking unit 29 is closed, such that the dosing chamber 25 is filled with the product again.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breath they are fairly, legally, and equitably entitled.

What is claimed is:

1. An infusion device for therapeutic use, comprising a waterproof covering which forms one of a casing, casing part or a container for storing the infusion device and monitoring means for monitoring the water-impermeability of the covering, the monitoring means comprising:
   a) a medium situated in the covering and having at least one physical or chemical parameter which changes in accordance with the impermeability of the covering, wherein the medium is a moisture-bonding medium, wherein the moisture-bonding medium is silicone gel; and
   b) information means which, if said parameter changes, automatically outputs an information signal, at least when the extent of the change signifies a loss of water-impermeability in the covering; and
   c) a moisture detector.

2. The infusion device according to claim 1, wherein the physical or chemical parameter is moisture, and wherein the moisture detector detects a change in a value of the physical or chemical parameter of the medium and feeds a detection signal to the information means in accordance with the value of the parameter, from which the information means forms the information signal.

3. The infusion device according to claim 1, wherein the monitoring means outputs the information signal in accordance with the time in which the value of the physical or chemical parameter changes to a predetermined extent.

4. The infusion device according to claim 1, wherein the medium absorbs moisture.

5. The infusion device according to claim 1, wherein the medium chemically reacts with water or water vapor.

6. The infusion device according to claim 5, wherein the chemical reaction results in a change of color.

7. The infusion device according to claim 6, wherein the change in color directly forms the information signal.

8. The infusion device according to claim 1, wherein the physical or chemical parameter is a change in color, wherein the moisture detector detects a change in a value of the physical or chemical parameter of the medium and feeds a detection signal to the information means in accordance with the value of the parameter, from which the information means forms the information signal.

9. The infusion device according to claim 1, wherein the physical or chemical parameter is moisture, and wherein the medium and the moisture detector is formed by a layer of the covering or by particles embedded in the covering thereby changing the electrical conductivity, capacitance or inductivity when contacted with moisture.

10. The infusion device according to claim 1, wherein the medium and the moisture detector are adjusted to each other such that the permeability is detected before a degree of moisture is reached in an inner space.

11. The infusion device according to claim 1, wherein the monitoring means further comprises a controller, an acoustic signal transmitter, a display, and a pump.

12. The infusion device according to claim 11, wherein the controller directs the acoustic signal transmitter such that the transmitter outputs an acoustic alarm signal which characterizes the loss of water-impermeability.

13. The infusion device according to claim 11, wherein the controller directs the display to indicate the loss of water-impermeability optically.

14. The infusion device according to claim 11, wherein the pump is connected to the surroundings by an air connection which is integrated in the covering.

15. The infusion device according to claim 1, wherein the monitoring means further comprises a controller, wherein the controller identifies whether the covering is impermeable based on a comparison between a value of a detection signal from the moisture sensor and a predetermined comparison value.

* * * * *

UNITED STATES PATENT AND TRADEMARK OFFICE
CERTIFICATE OF CORRECTION

PATENT NO. : 8,728,060 B2
APPLICATION NO. : 13/165200
DATED : May 20, 2014
INVENTOR(S) : Kurt Friedli et al.

Page 1 of 1

It is certified that error appears in the above-identified patent and that said Letters Patent is hereby corrected as shown below:

On the Title Page

Item (57) "ABSTRACT
The invention relates to an infusion device for therapeutic use comprising a water-tight cover in the form of a housing, a housing part or a receptacle for holding said infusion device and a control system which is used for controlling the cover water tightness and comprises c) a medium arranged in the cover and characterized by at least one physical or chemical quantity variable according to the cover water tightness and d) an information system which automatically transmits at least one information signal when said quantity changes in such a way that the loss of the cover water tightness is indicated."

should read

Item (57) --ABSTRACT
The invention relates to an infusion device for therapeutic use comprising a water-tight cover in the form of a housing, a housing part or a receptacle for holding said infusion device and a control system which is used for controlling the cover water tightness and comprises a medium arranged in the cover and characterized by at least one physical or chemical quantity variable according to the cover water tightness and an information system which automatically transmits at least one information signal when said quantity changes in such a way that the loss of the cover water tightness is indicated.--

Signed and Sealed this
Seventeenth Day of March, 2015

Michelle K. Lee
*Director of the United States Patent and Trademark Office*